United States Patent

Ofner

[19]

[11] Patent Number: 5,971,540
[45] Date of Patent: Oct. 26, 1999

[54] MAGNIFYING SPECTACLES WITH VARIABLE FOCUS, VARIABLE MAGNIFICATION FACTOR AND AUTOMATIC PARALLAX COMPENSATION

[75] Inventor: Anton Gerald Ofner, Vienna, Austria

[73] Assignee: Olympus Austria Gesellschaft, Vienna, Austria

[21] Appl. No.: 09/036,335

[22] Filed: Mar. 6, 1998

Related U.S. Application Data

[63] Continuation-in-part of application No. 08/648,127, Jun. 7, 1996, abandoned.

[51] Int. Cl.$^6$ .................................................. G02C 1/00
[52] U.S. Cl. ........................................................ 351/158
[58] Field of Search ............................ 351/200, 237, 351/239, 243, 57, 59, 158; 396/121, 123; 359/481

[56] References Cited

U.S. PATENT DOCUMENTS

| | | | |
|---|---|---|---|
| 3,458,246 | 7/1969 | Krebs . | |
| 3,865,468 | 2/1975 | Holcomb | 350/146 |
| 4,195,918 | 4/1980 | Freche et al. | 351/158 |
| 4,395,731 | 7/1983 | Schoolman | 358/88 |
| 4,787,734 | 11/1988 | Matsumura | 351/212 |
| 4,807,985 | 2/1989 | Feinbloom | 351/158 |
| 4,865,438 | 9/1989 | Wada | 351/158 |
| 4,912,388 | 3/1990 | Tanaka et al. | 318/640 |
| 4,929,075 | 5/1990 | Eliakim | 351/158 |
| 5,078,469 | 1/1992 | Clark et al. | 359/481 |
| 5,374,820 | 12/1994 | Haaksman | 250/201.6 |
| 5,422,700 | 6/1995 | Suda et al. | 396/123 |
| 5,483,305 | 1/1996 | Kohayakawa | 351/243 |

FOREIGN PATENT DOCUMENTS

| | | |
|---|---|---|
| 98 782 | 2/1993 | Austria . |
| 1 165 899 | 3/1964 | Germany . |
| 37 20 190 | 12/1987 | Germany . |
| 40 04 248 | 8/1990 | Germany . |
| 93 03 663 U | 6/1993 | Germany . |
| 1-180508 | 7/1989 | Japan . |

Primary Examiner—George Manuel
Attorney, Agent, or Firm—Walter C. Farley

[57] ABSTRACT

Magnifying spectacles for surgical use have an automatic focusing device, a device for automatically altering the magnification factor and a device for automatic parallax compensation corresponding to the current focal length. During surgical operations, alteration of the working distance is commonly necessary due to the positions of different operating sites. Automatic adaptation of the focal length and the parallax angle allows optimum optical configuration to be reached without the need for the surgeon to use his hands. Focusing can be adjusted using a foot switch.

4 Claims, 4 Drawing Sheets

MAGNIFYING SPECTACLES WITH VARIABLE FOCUS, VARIABLE MAGNIFICATION FACTOR AND AUTOMATIC PARALLAX COMPENSATION

CROSS-REFERENCE TO RELATED APPLICATION

This application is a continuation-in-part of application Ser. No. 08/648 127 filed Jun. 7, 1996, now abandoned.

FIELD OF THE INVENTION

This invention relates to magnifying spectacles with variable magnification and with a device for automatically altering the focal length which is coupled to a device for automatically matching the parallax to the current focal length.

BACKGROUND OF THE INVENTION

Magnifying spectacles have their principal application in those surgical areas in which an operating microscope cannot be used for technical and anatomical reasons but in which unaided human vision is inadequate to enable the surgeon to see adequately the field of surgery. This problem arises commonly in vascular surgery and neurosurgery. It is frequently desirable or even necessary during an operation to alter the working distance, i.e., the distance between the eyes and the operating point and/or the magnification factor with which the operating point is being observed. Known operating or magnifying spectacles either do not satisfy this requirement, or they do so only incompletely. No magnifying spectacles are known from the prior art which have means for automatically altering the focal length with parallax compensation and also means for altering or adjusting the magnification factor. Reference is made in this connection to the following documents which are briefly discussed below.

| D1 | AT | E98 782B |
| D2 | US | 4 865 438 |
| D3 | US | 4 807 985 |
| D4 | DE | 37 20 190 |
| D5 | US | 5 078 469 |

Document D1 relates to magnifying spectacles for surgical purposes with a device for automatically altering the focal length of the spectacles and the focal length adjustment is mechanically coupled to a device for automatically matching the parallax to the current focal length. The determination of the current distance of the spectacles to the subject is made by ultrasound or light sensors.

Document D2 also relates to magnifying spectacles, particularly for surgical purposes, whose focal length is automatically adjusted to the current distance of the subject. The distance determination is accomplished as in D1.

Documents D3 and D4 disclose telescopic spectacles for people with impaired vision for viewing near and remote objects. The spectacles in accordance with D3 have devices for automatically matching the focal length and for matching the angle of inclination to the position of the head of the user. Spectacles in accordance with D4 have manually operable devices for altering the focal length (slide-in prisms) and for parallax compensation (actuating lever).

Magnifying spectacles for surgical purposes disclosed in document D5 are equipped with a video camera which has a zoom lens system and permits not only photographic recordal but also the transfer of the field of view of the operator, which is illuminated by means of a fiber optic system, to remote stations.

When one is using fixed focus spectacles in certain situations, such as work in the stomach cavity, the user must move his head closer to the open stomach wall due to the requirement for a constant spacing between the eyes and the working field and thus moves, on the one hand, into an ergonomically undesirable body attitude and, on the other hand, obstructs the field of view of assisting doctors with his head, thus making the provision of assistance more difficult. Magnifying spectacles with manually adjustable focus also do not help in this connection because, for sterility reasons, the focus can only be adjusted before, but not during, an operation.

SUMMARY OF THE INVENTION

It is important to recognize that when focus and parallax in a binocular optical device are adjusted together, the person looking through the device will always see a sharp image. If parallax is not adjusted as focus changes, the focus may be sharp on some objects but not so sharp on others. Because the human brain tries to compensate for this, the viewer may have feelings of sickness which is, at the least, distracting.

An object of the present invention is to eliminate the aforementioned disadvantages by providing magnifying spectacles which have devices for automatically adjusting the focal length of the spectacles while also matching the spectacle parallax to the current focal length.

In a preferred construction of the invention, means for smoothly adjusting the focus and parallax is connected to a foot switch and magnification is controlled separately, either by the foot switch or other means. A measuring scale matched to the current magnification factor for precise determination of the sizes of objects can be made visible in the focus plane.

Briefly described, the invention comprises a magnifying surgical spectacle system comprising first and second optical systems for concurrent use with right and left eyes, each optical system having a lens system with a movable part for focus adjustment and movable parts for zoom adjustment, the first and second optical systems being connected for relative swiveling movement to adjust parallax between the systems. Drive means concurrently changes the zoom adjustment in the first and second optical systems. The spectacle system has means for changing the parallax adjustment between the optical systems and means for changing focus adjustments of the optical systems. A single drive motor changes focus and parallax; and a mechanical coupling is provided between the means for changing parallax adjustments and the means for changing focus adjustments so that the single motor concurrently changes focus and parallax.

BRIEF DESCRIPTION OF THE DRAWINGS

Examples of devices in accordance with the invention will be described with reference to the accompanying drawings wherein.

DESCRIPTION OF PREFERRED EMBODIMENTS

A spectacle system in accordance with the invention comprises a housing indicated by the dashed lines at 20 containing two lens systems, one for each eye of the user. This apparatus is provided with some sort of head mounting, not shown, which is conventional in the field and may comprise a head band or a more complex framework fitting the head.

Figure 1:
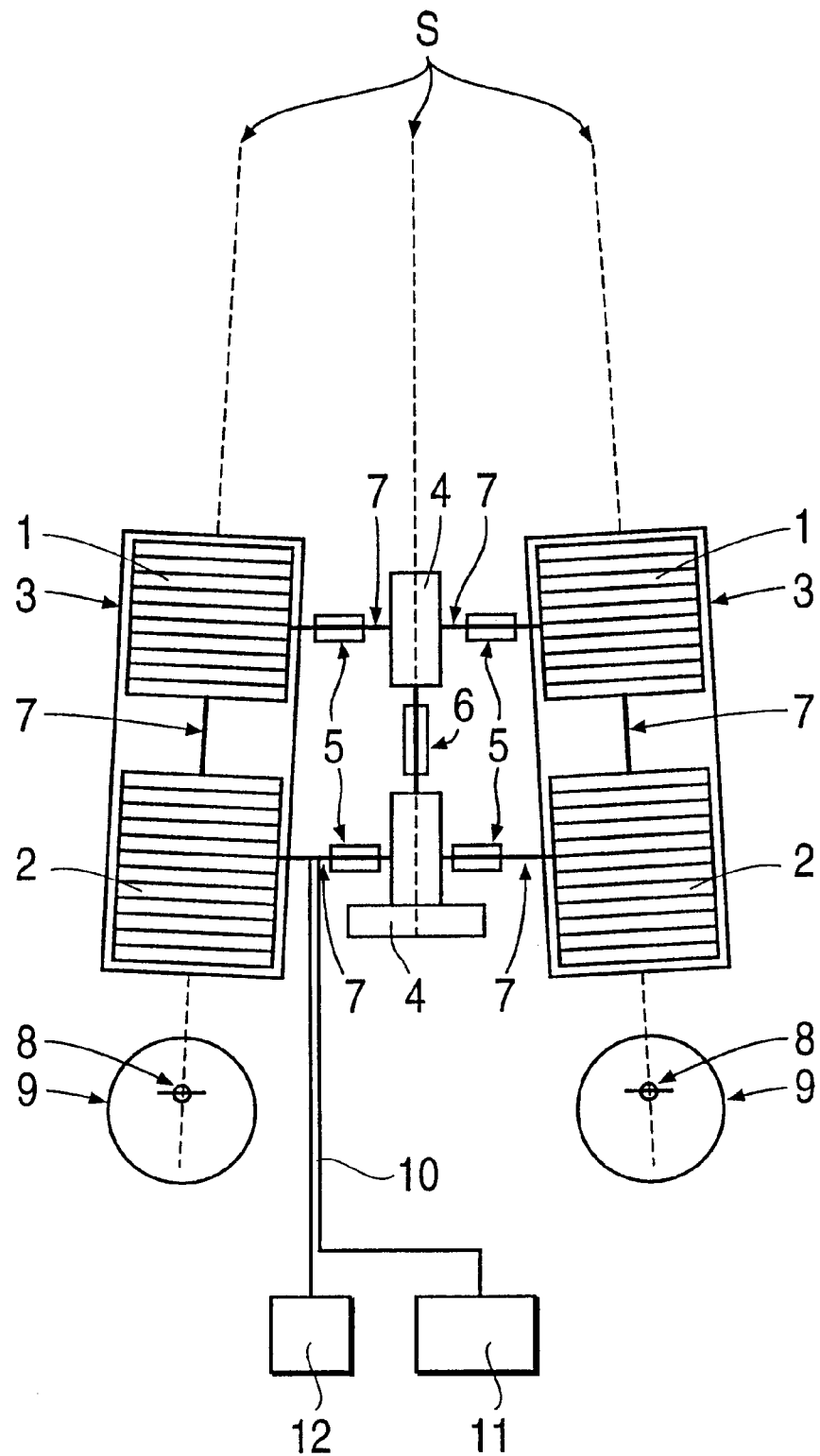
FIG. 1 is a schematic diagram of a first embodiment of magnifying spectacles in accordance with the invention with alteration of the focal length coupled to a device for automatically matching the parallax to the current focal length.
Figure 2:
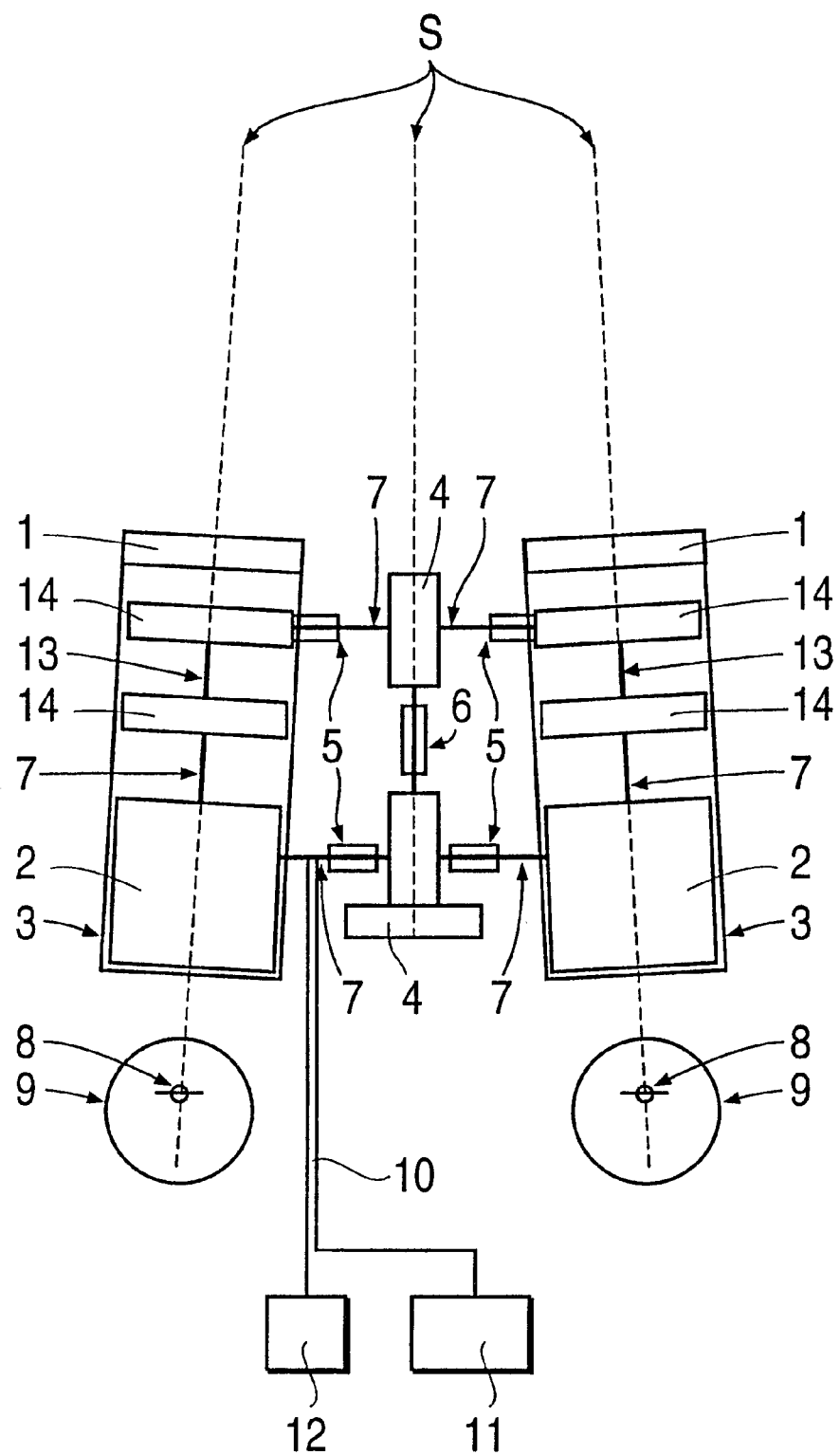
FIG. 2 is a schematic diagram of a further embodiment of magnifying spectacles in accordance with the invention having a zoom lens system incorporated therein.
Figure 3:
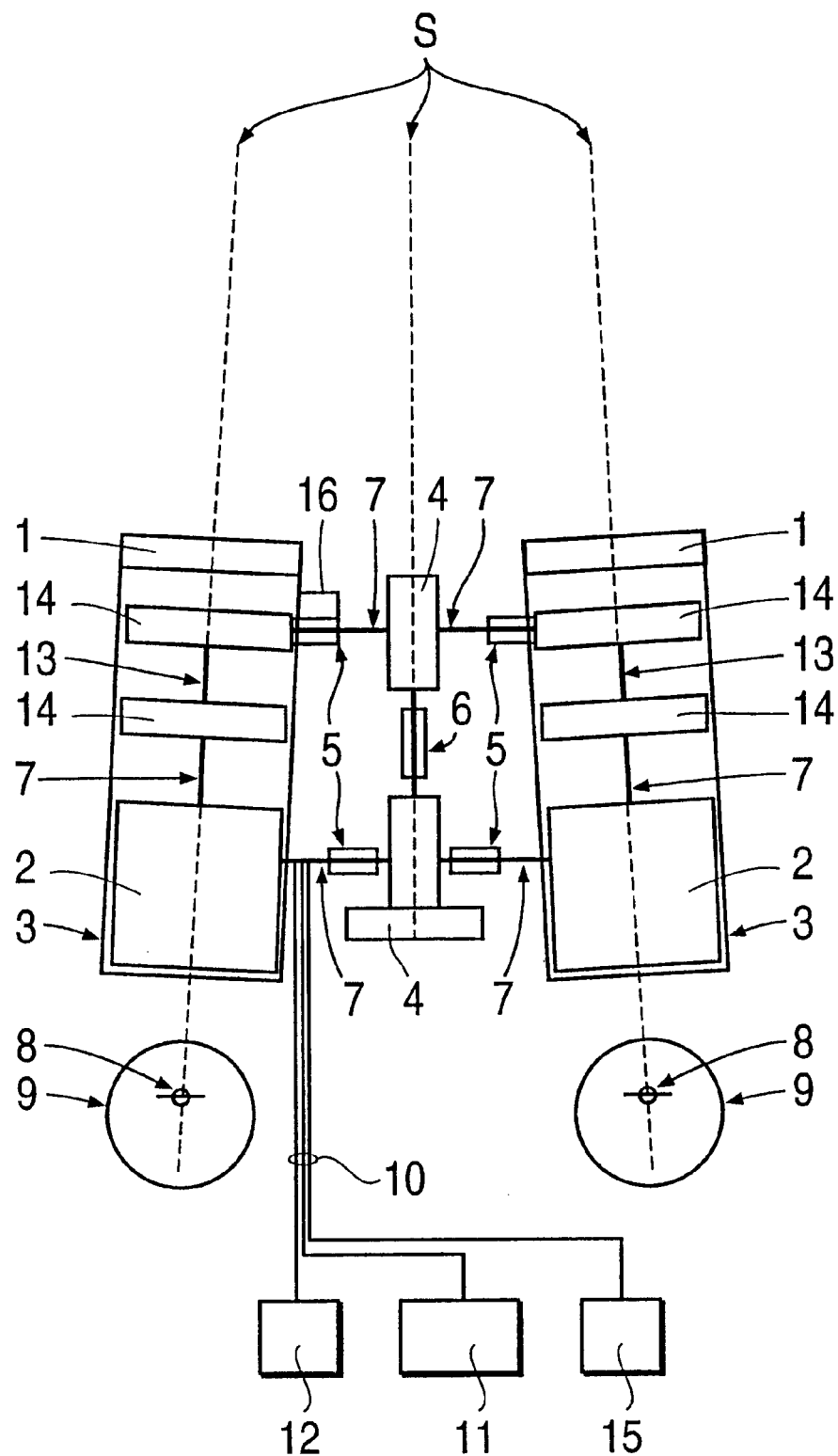
FIG. 3 is a schematic diagram of another embodiment of magnifying spectacles in accordance with the invention with voice-controlled adjustment of the focal length and magnification factor of the spectacles.

The lens systems shown in the embodiments of FIGS. 1–3 each comprise an objective 1 and an eyepiece 2 and the lens systems are housed in two tubes 3. In or between tubes 3 are an autofocusing device 4 and means comprising electric motors 5 and 6 for parallax compensation when the focal length alters and means for altering the focal length itself, and the associated positioning mechanisms 7. This ensures that the optical axes S in each tube position pass through projection centers 8, i.e., through the optical center points of the eyes 9 of the user. An electrical multiconductor cable 10 connects the magnifying spectacles to a foot switch 11. Actuation of the foot switch selectively controls the focal length and also the magnification factor. For this purpose, the foot switch can be provided with two or more separately operable portions, which can be similar to a foot switch of the type used with an audio transcribing machine, permitting the user to adjust the magnification and focal length selectively and at will.

An external control unit 12, which can be mounted on the head mounting of the spectacles or on the belt of the user, for example, includes a power supply for the mechanisms of the magnifying spectacles and a semiconductor device, such as an integrated circuit processor "chip", for controlling the motors and for calculating the proper positions for the optical elements. For example, the processor chip can calculate the angle of the optical axes relative to each other which is required at the current active working distance and the positions of the lenses in the objectives 1 and eyepiece 2, and then positions then with the aid of positioning mechanisms 5 and 6.

The magnifying spectacles of FIG. 2 are constructed as zoom spectacles and are therefore equipped with a zoom lens system 13 in objective 1 and the associated zoom mechanism 14.

FIG. 3 is an example of magnifying spectacles having a voice control module 15 with a microphone 16.

Figure 4:
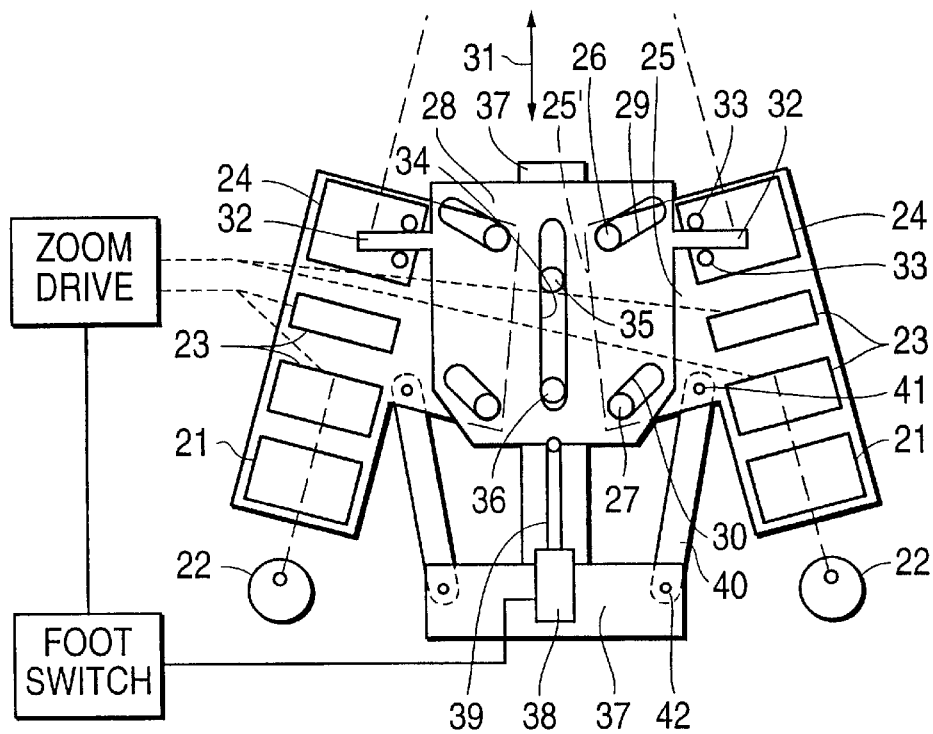
FIGS. 4 and 5 are schematic diagrams of a further embodiment of magnifying spectacles in accordance with the invention showing in more detail the mechanism for accomplishing the parallax and focal length adjustments.
Figure 5:
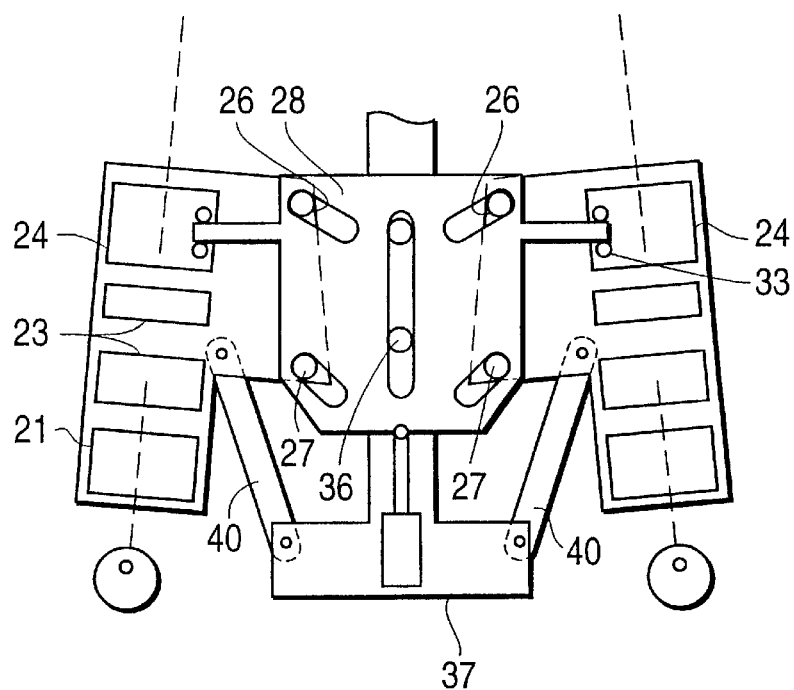

FIGS. 4 and 5 show in more detail a drive system for concurrently changing focus and parallax, the components thereof being shown in two possible positions. In these figures, on each side of the magnifying spectacles is an optical system including an ocular lens system 21 near eye 22, two zoom adjustment lens elements 23, and an objective lens system 24. Each optical system is housed in a tubular housing. Ocular lens system is fixed in the housing. Zoom systems 23 are movable axially by a zoom drive 50 mechanically coupled to lens elements 23, the zoom drive being schematically shown as a box in FIGS. 4 and 5, through a suitable gear mechanism, not shown. Objective system 24 is axially movable for focus adjustment.

A drive plate 25 is attached to each optical housing tube containing the lens systems. The inner, central limits of plates 25 are shown at 25' as a dashed line. Each drive plate lies in a plane substantially parallel to the plane of the drawing and carries two guide pins 26 and 27 which are perpendicular to the plate. A slot plate 28 lies between the two optical system housings and overlaps and is parallel with drive plates 25. Slot plate 28 is penetrated by two pairs of slots 29 and 30 which receive and guide pins 26 and 27, respectively. It will be noted that each slot 29 and 30 is an elongated slot having substantially parallel sides which form an acute angle with a central bisector of the optical systems and that the sides of slot 29 make a smaller acute angle with the bisector than do the sides of slot 30.

Slot plate 28 is movable longitudinally and bidirectionally in the directions of arrow 31. When the slot plate is moved, the two optical systems pivot about two pivot points which lie outside the apparatus itself and are preferably within the eyes of the user. As seen in FIG. 4, when the slot plate is moved away from eyes 22, the angle between the two optical axes is increased for focusing on an object which is nearer, whereas when the plate is moved toward the eyes, the angle becomes smaller for focusing on a point farther away.

On each side of slot plate 28 an arm 32 extends outwardly away from the plate and extends between a pair of guide stops 33 coupled to lens system 24. Thus, whenever plate 28 moves longitudinally to adjust the parallax as described above, the focal length is also adjusted.

It is necessary for slot plate 28 to be guided parallel with the centerline of the optical systems as it is moved in the manner described above so that it does not rotate. For this purpose, slot plate 28 has a central longitudinal guide slot 34 along the center line of the system, parallel with the central bisector, through which two pins 35 and 36 which are carried by an anchor plate 37, shown as a generally T-shaped member, which can be part of housing 20 of the spectacle headset apparatus worn by the user.

A motor 38 with an output push rod 39 is attached to a transverse portion of anchor plate 37 and rod 39 is attached to slot plate 28. When energized, motor 38 drives rod 39 to move plate 28 forward and backward in the directions of arrow 31. Reaction arms 40 are pivotally mounted at one end on drive plates 25 and at the other ends at anchor plate 37. These arms provide movable pivot points about which plates 25 and the optical systems are swivelled rather than simply being moved back and forth by the motor drive and plate 28.

Energization of motor 38 can be controlled by a foot switch 51, as described above, or by an autofocus system with a distance measurement system using, e.g., infrared distance measurement and a computer control.

The details of construction can be altered, for example, by coupling the drive of the lens systems 24 to plate 28 with an equivalent system using cables pulled around rollers.

What is claimed is:

1. A magnifying surgical spectacle system comprising
first and second optical systems for concurrent use with right and left eyes, each optical system having a lens system with a movable part for focus adjustment and movable parts for zoom adjustment;
means for pivotally connecting said first and second optical systems for relative swiveling movement to adjust parallax between said systems;

drive means for concurrently changing said zoom adjustment in said first and second optical systems;

means for changing said parallax adjustment between said optical systems;

means for changing focus adjustments of said optical systems;

a single drive motor for changing focus and parallax; and mechanical coupling means between said means for changing parallax adjustments and said means for changing focus adjustments whereby said single motor concurrently changes focus and parallax.

2. A system according to claim 1 wherein said mechanical coupling means comprises a plate driven by said single drive motor along a central axis of said optical systems, said plate carrying said means for changing said parallax adjustment and said means for changing focus.

3. A system according to claim 2 wherein said means for changing focus comprises a slot and pin coupling engaging said optical system at each of two sides of said plate.

4. A system according to claim 1 and including a foot switch for actuating said single drive motor.

* * * * *